(12) United States Patent
Tomarchio et al.

(10) Patent No.: US 7,605,096 B2
(45) Date of Patent: Oct. 20, 2009

(54) FLUSHABLE HARD SURFACE CLEANING WET WIPE

(75) Inventors: Vincenzo Tomarchio, Alcamo (IT); Andrea Piccini, Rome (IT)

(73) Assignee: The Procter & Gamble Company, Cincinnati, OH (US)

( * ) Notice: Subject to any disclaimer, the term of this patent is extended or adjusted under 35 U.S.C. 154(b) by 418 days.

(21) Appl. No.: 09/887,887

(22) Filed: Jun. 22, 2001

(65) Prior Publication Data

US 2002/0031966 A1   Mar. 14, 2002

(30) Foreign Application Priority Data

Jun. 23, 2000   (EP)   ................... 00870142

(51) Int. Cl.
*B32B 27/04* (2006.01)
*B32B 27/12* (2006.01)
*B32B 5/02* (2006.01)

(52) U.S. Cl. .................. 442/123; 422/165; 422/408

(58) Field of Classification Search ................ 442/123, 442/165, 408
See application file for complete search history.

(56) References Cited

U.S. PATENT DOCUMENTS

| 4,117,187 | A | * | 9/1978 | Adams et al. | 442/118 |
|---|---|---|---|---|---|
| 4,725,489 | A | * | 2/1988 | Jones et al. | 442/121 |
| 4,755,421 | A | * | 7/1988 | Manning et al. | 442/338 |
| 4,941,995 | A | * | 7/1990 | Richards | 252/407 |
| 5,049,440 | A | * | 9/1991 | Bornhoeft et al. | 442/123 |
| 5,888,524 | A | | 3/1999 | Cole | |
| 6,716,805 | B1 | * | 4/2004 | Sherry et al. | 510/295 |

FOREIGN PATENT DOCUMENTS

| EP | 0 211 773 A2 | 2/1987 |
|---|---|---|
| EP | 0 113 254 B1 | 10/1987 |
| EP | 0 233 943 B1 | 6/1992 |
| EP | 0 602 881 B1 | 7/1998 |
| WO | WO 89/05114 | 6/1989 |

* cited by examiner

*Primary Examiner*—Norca L Torres-Velazquez
(74) *Attorney, Agent, or Firm*—Jason J. Camp; Thibault Fayette; Brent M. Peebles

(57) ABSTRACT

According to the present invention there is provided a wet wipe comprising a substrate that has tensile strength of at least 5 N/inch and which is biodegradable. In a further aspect, the present invention provides a flushable wet wipe comprising a substrate having a loading factor of at least 1.5 grams of cleaning composition per gram of substrate and which is biodegradable. The wet wipes is suitable for cleaning hard surfaces, especially lavatories and is flushable.

25 Claims, No Drawings

FLUSHABLE HARD SURFACE CLEANING WET WIPE

TECHNICAL FIELD

The present invention relates to a wet wipe suitable for cleaning hard surfaces, which has sufficient wet strength to remain intact during the cleaning action, but which is also sufficiently biodegradable as to be suitable for flushing. The wipes according to the present invention are especially suitable for cleaning bathroom and kitchen surfaces.

BACKGROUND

Wet wipes are typically pre-moistened, disposable towelettes which may be utilised in a variety of applications both domestic and industrial and perform a variety of functions. Wet wipes are typically used to wipe inanimate surfaces, and may provide numerous benefits such as cleaning, cleansing, and disinfecting.

One particular application for wet wipes is wiping and/or cleaning surfaces and the application of compositions to surfaces, for example kitchen and bathroom surfaces, spectacles, shoes and surfaces which require cleaning in industry, for example surfaces of machinery or vehicles.

Wet wipes are commonly constructed from webs of combinations of synthetic, man-made and natural fibres, such as polyolefin fibres, viscose fibres, cotton fibres, which are generally moistened with an aqueous composition which may contain amongst others ingredients surfactants, preservatives, oils and scents depending on the end use envisaged.

A variety of webs and liquid compositions suitable for application to such webs are known and disclosed in the art listed below. Typically the webs require a binder in order to provide strength to the web, in particular when wet.

WO 89/05114 discloses disposable wipes for hard surface cleaning which are impregnated with a liquid composition and EP 0 211 773 discloses a cloth for polishing a car. EP 0 113 254 discloses an antimicrobial non-woven fabric. The fabric may be provided from natural or synthetic fibres or blends thereof. According to the disclosed invention an antimicrobial agent is selected which forms a colloidal suspension with a given conventional binder.

EP 0 233 943 discloses a non-woven wet wipe which is said to be antimicrobially active. In a preferred embodiment the web for the wet wipes is provided from wood pulp and comprises a non-acrylate binder (ethylene vinyl acetate). The wet wipes further comprise an antimicrobial agent, which is mixed into the binder and applied to the non-woven web therewith.

U.S. Pat. No. 5,888,524 discloses an antimicrobial composition for use with conventional wet wipes and lotions. The wet wipes can be provided from synthetic or natural fibres or a combination thereof. According to the disclosed invention the wet wipes are saturated with a rather high amount of the antimicrobial composition, indeed, it is taught that the weight of the lotion should be up to 6 times the weight of the dry wipe.

Traditionally, hard surface cleaning wipes have been made using synthetic fibres since only synthetic fibres provide sufficient strength in the wipe for it to withstand the stress and strain of the cleaning action. Wipes made using natural and/or synthetic fibres have generally been much weaker in terms of tensile strength and have required the use of a binder or wet strength agent to increase the tensile strength to a level suitable to withstand the cleaning action. EP 0 602 881 discloses a wet wipe comprising wood pulp and man-made fibres made preferably for use in personal hygiene, for example as moist toilet paper. The wipes also comprise a wet strength agent, for example polyacrylamide, to improve the wet strength of the wipe.

Synthetic wipes and those wipes comprising a binder suffer the disadvantage of being less biodegradable than wipes made using natural fibres, to the point where they are not suitable for flushing down a lavatory since they may cause blockages in drains and/or septic tanks. It is therefore the object of the present invention to provide a wet wipe that is sufficiently strong to be suitable for cleaning hard surfaces, but which is also sufficiently biodegradable such that it can be safely flushed down a lavatory.

A further object of the present invention has been to find a wet wipe substrate that is suitable for flushing down a lavatory but which can also sustain a high cleaning composition loading factor without adversely affecting either the tensile strength or absorbency of the wipe.

SUMMARY OF THE INVENTION

According to the present invention there is provided a flushable wet wipe suitable for cleaning a hard surface comprising a substrate having tensile strength of at least 5 N/inch and which is biodegradable.

According to a further aspect of the present invention there is provided a flushable wet wipe suitable for cleaning a hard surface comprising a cleaning composition and a substrate, wherein the substrate has a loading factor of at least 1.5 grams of cleaning composition per gram of substrate and is biodegradable.

DETAILED DESCRIPTION OF THE INVENTION

The wet wipe of the present invention comprises a substrate which has tensile strength, even when wet of greater than 5 N/inch, but yet is also biodegradable.

Tensile Strength can be measured according to known techniques. Tensile strength herein is measured according to standard European Disposable Absorbent Non-woven Association (EDANA) Industry Methodology, reference method #20.2-89.

The substrate of the present invention has tensile strength measured in either the machine direction or the cross direction of at least 5 N/inch. Machine direction is defined as the direction in which the substrate moves through the manufacturing machine. The Cross direction is defined as the direction perpendicular to the machine direction. In a preferred embodiment the tensile strength of the substrate is at least 8 N/inch and most preferably at least 10 N/inch measured in either the machine or cross direction. Even more preferably the substrate is designed such that the tensile strength measured in the machine direction is higher than in the cross direction. Such a design therefore takes into account the additional tension that is placed on the wipe during dispensing of the individual wipe.

In an alternative embodiment of the present invention, the substrate of the present invention is designed such that it can retain enough cleaning composition for the wipe to be used as an efficient cleaning tool, yet still be biodegradable and preferably also have sufficient absorption and tensile strength when wet to withstand the stress and strain of the cleaning action. Hence according to the present invention the wet wipe comprises a substrate which has a loading factor of at least 1.5 grams of cleaning composition per gram of substrate, but yet is also biodegradable. Preferably the substrate has a loading factor of at least 2 grams, more preferably at least 2.8 grams of cleaning composition per gram of substrate. Loading factor is expressed as the weight ratio of cleaning composition loaded onto the substrate and the substrate. In this embodiment it is also preferred that the substrate has tensile strength of at least 5 N/inch, more preferably at least 8 N/inch and most preferably at least 10 N/inch measured in either the machine or cross direction.

In a further aspect the substrate of the present invention has absorption capacity of at least 6 grams of water per gram of substrate, more preferably at least 8, most preferably at least 8.5 grams of water per gram of substrate. Absorption capacity is measured according the standard EDANA non-woven industry methodology reference method number 10.3-99.

The substrate of the present invention is capable of biodegrading by disintegration in anaerobic conditions within a short period of time. Anaerobic disintegration is measured according to a test method which simulates the anaerobic disintegration environment in a septic tank or a sewage treatment facility. During the test the wipes are exposed to biologically active anaerobic sludge over a period of 4 weeks and the percent disintegration is measured by weight loss over time.

Test Method

Anaerobic sludge is obtained from a sewage treatment facility that handles predominantly residential waste. The anaerobic sludge is screened through a 18 mesh screen to remove any particles larger than 1 mm. A reactor bottle is partially filled with 1.5 L of sludge, at least 15 g/L of which is solids and the pre-weighed sample of a wipe. The bottle is then sealed with a one-hole stopper which allows venting of effluent gases. The bottle is placed in a 35° C. incubator for the duration of the test. The reactor bottle is mixed daily by inverting several times to keep the samples in the sludge. Samples are removed from duplicate reactor bottles over time. The sample is poured onto an 18 mesh sieve and then rinsed under running tap water. Any sample residue that remains on the screen is gently rinsed off and placed in a beaker to dry in the oven at 40° C. overnight. Cooled, dried samples are weighed to calculate percent weight loss.

Samples are deemed to be biodegradable if at least 95% disintegration in anaerobic conditions is achieved after 4 weeks of anaerobic digestion. In a preferred embodiment of the present invention at least 97%, more preferably substantially 100% disintegration in anaerobic conditions is achieved after 4 weeks of anaerobic digestion.

Furthermore, the substrate of the present invention is also biodegradable in aerobic conditions. Aerobic biodegradation is measured according to the American Society for Testing and Materials ASTM) method D5271-93 which is a standard test method for determining the aerobic biodegradation in an activated-sludge-wastewater-treatment system.

Substrate

The substrate is preferably provided by a web, typically as a sheet of material cut from the web. The web may be woven or non-woven, foam, sponge, battings, balls, puffs or films. Most preferably the web is non-woven and comprises manmade fibers, even more preferably the web comprises solely man-made fibres.

According to the present invention the web may be produced by any method known in the art. For example nonwoven material substrates can be formed by dry forming techniques such as carding, air-laying or wet laying, such as on a paper making machine. Other non-woven manufacturing techniques such as melt blown, spun bonded, needle punched, spun laced may also be used. Preferably the web used in the present invention is produced using the carding method, during which entangled fibrous mats are transformed into parallel fibrous webs.

While various embodiments of a web, to provide a substrate, are within the scope of the present invention and are detailed below, in a preferred embodiment the web is carded and non-woven comprising man-made fibres. In a preferred embodiment the web comprises at least 95%, even more preferably at least 97% and most preferably approximately 100% man-made fibres.

Man-made fibres, as used herein, includes fibres manufactured from cellulose, for example derivatives of or regenerated cellulose and thus are distinguishable from synthetic fibres, which are based on synthetic organic polymers. A derivative fibre, as used herein, is a fibre formed when a chemical derivative of a natural polymer, e.g., cellulose, is prepared, dissolved, and extruded as a continuous filament, and the chemical nature of the derivative is retained after the fibre formation process. A regenerated fibre, as used herein, is a fibre formed when a natural polymer, or its chemical derivative, is dissolved and extruded as a continuous filament. Whilst the physical nature of the natural polymer is changed, the chemical nature of the natural polymer is substantially retained or regenerated after the fibre formation process. Preferred man-made fibres have a denier of 0.5 dtex to 3.0 dtex, more preferably of 1.0 dtex to 2.0 dtex, most preferably of 1.5 dtex to 2.0 dtex.

Preferred man-made fibres used in the present invention include rayon (viscose) that is produced by dissolving cellulose fibres in N-methylmorpholine-N-oxide, resulting in what is known as regenerated cellulosic fibres and which are supplied by Tencel Fibres Europe, UK.

Man-made fibres are preferred fibres for use in webs of the present invention due to their high consumer acceptance and their cheap and typically ecological production. Man-made fibres and in particular cellulose derived man-made fibres, are known to exhibit high biodegradability, however it had not previously been realised that webs made entirely or substantially entirely of man-made fibres could be suitable for use as a wet wipe substrate. Wet wipes composed of man-made fiber web substrates provide further advantages in that the fibres used can also be chemically or physically altered during the fiber formation process so as to comprise further advantageous benefits such as softness, roughness and absorbency.

The web preferably has a weight of at least 20 $gm^{-2}$ and preferably less than 150 $gm^{-2}$, and most preferably the base weight is in the range of 20 $gm^{-2}$ to 100 $gm^{-2}$, more preferably from 40 $gm^{-2}$ to 70 $gm^{-2}$. The web may have any caliper. Typically, when the web is made by an air laying process, the average web caliper is less than 1.0 mm. More preferably the average caliper of the web is from 0.2 mm to 0.9 mm. The web caliper is measured according to standard EDANA Non-woven Industry Methodology, reference method #30.4-89.

In addition to the fibres used to make the web, the web can comprise other components or materials added thereto as known in the art, to improve appearance, surface texture, colour, and odour. An example is the use of opacifying agents, for example titanium dioxide.

In order to achieve the strength requirement of one embodiment of the wet wipe substrate, the fibres are hydroentangled. Hydroentanglement is a process whereby fibers of the web are rearranged and entangled by means of fluid forces. Hydroentanglement can in this way be used as a bonding means, repositioning and entangling individual fibers into configurations that bring about frictional interlocking at the fiber level. In addition to the bonding benefits, hydroentanglement can also be used to provide surface texturing, whereby hydroentanglement repositions fibers into open-patterned arrangements. Webs that have undergone a hydroentanglement treatment, contain no chemical binders, and have not been thermally bonded. Hydroentangled non-woven webs are mechanically strong, can withstand stretching, pulling and abrasion, but can are be made to be tactil and soft. Furthermore the absorbency and wetting capability of the web is not adversely affected by the hydroentanglement process.

Hence according to the present invention the substrate of the most preferred embodiment is composed of substantially 100% hydroentangled man-made regenerated cellulosic fibres.

According to a preferred embodiment of the present invention the substrate incorporates a cleaning composition as described herein. By "incorporates" it is meant herein that said substrate or wet wipe is coated or impregnated with a preferably liquid cleaning composition as described herein.

In preparing wet wipes according to the present invention, the composition is applied to at least one surface of the substrate material. The composition can be applied at any time during the manufacture of the wet wipe. Preferably the composition can be applied to the substrate after the substrate has been dried. Any variety of application methods that evenly distribute lubricious materials having a molten or liquid consistency can be used. Suitable methods include spraying, printing, (e.g. flexographic printing), coating (e.g. gravure coating or flood coating) extrusion whereby the composition is forced through tubes in contact with the substrate whilst the substrate passes across the tube or combinations of these application techniques. For example spraying the composition on a rotating surface such as calender roll that then transfers the composition to the surface of the substrate. The composition can be applied either to one surface of the substrate or both surfaces, preferably both surfaces. The preferred application method is extrusion coating.

The composition can also be applied uniformly or non uniformly to the surfaces of the substrate. By non uniform it is meant that for example the amount, pattern of distribution of the composition can vary over the surface of the substrate. For example some of the surface of the substrate can have greater or lesser amounts of composition, including portions of the surface that do not have any composition on it. Preferably however the composition is uniformly applied to the surfaces of the wipes.

Preferably, the composition can be applied to the substrate at any point after it has been dried. For example the composition can be applied to the substrate preferably after calendering and prior to being wound up onto a parent roll. Typically, the application will be carried out on a substrate unwound from a roll having a width equal to a substantial number of wipes it is intended to produce. The substrate with the composition applied thereto is then subsequently perforated utilising standard techniques in order to produce the desired perforation line. Alternatively the substrate may be unwound from a roll, perforated to form wipes of the correct size, folded and then the composition is applied to the substrate.

Composition

The composition of the present invention is preferably suitable for use as a cleaning and/or disinfecting composition. The compositions may be formulated in any suitable form for example as a solid, paste or liquid. In the case where the compositions according to the present invention are formulated as solids, they can be applied to the substrate as a solid or alternatively can be mixed with an appropriate solvent, typically water, before application to the substrate. Where the composition is in liquid form, the compositions are preferably but not necessarily formulated as aqueous compositions. Liquid compositions are preferred herein for convenience of use.

In a preferred embodiment the liquid compositions according to the present invention are aqueous compositions typically comprising from 50% to 99.9% by weight of the total composition of water, preferably from 70% to 99% and more preferably from 80% to 99%. These aqueous compositions preferably have a pH as is of not more than 13.0, more preferably from 1 to 11, and most preferably from 2 to 10. The pH of the compositions can be adjusted by using organic or inorganic acids, or alkalinising agents, such as sodium hydroxide.

Compositions suitable for use as a cleaning composition preferably have pH in the range of from 5 to 13, more preferably from 7 to 13 and most preferably from 8 to 10. Compositions for use as disinfecting compositions preferably have a pH in the range of from 0 to 7, more preferably from 1 to 5 and most preferably from 2 to 4.

The compositions herein may comprise a variety of ingredients including, but not limited to peroxygen bleach, disinfecting components, organic acids, surfactants, chelants, solvents, builders, stabilisers, bleach activators, soil suspenders, dye transfer agents, brighteners, perfumes, anti dusting agents, enzymes, dispersant, dye transfer inhibitors, pigments, perfumes, radical scavengers, pH buffers, dyes or mixtures thereof.

Surfactant System

According to the present invention the substrate preferably incorporates a composition comprising a surfactant system. The surfactant system consists of a synergistic system comprising at least three surfactants, namely an anionic, a non-ionic and an amphoteric and/or zwitterionic surfactant.

The compositions preferably comprises the surfactant system at a level by weight of the total composition of from 0.05-20%, more preferably from 0.1-5% and most preferably from 0.2-3%.

Anionic Surfactant

Suitable anionic surfactants for use herein include alkyl sulphates. Suitable alkyl sulphates for use herein include water-soluble salts or acids of the formula $ROSO_3M$ wherein R is a $C_6$-$C_{24}$ linear or branched, saturated or unsaturated alkyl group, preferably a $C_8$-$C_{20}$ alkyl group, more preferably a $C_8$-$C_{16}$ alkyl group and most preferably a $C_{10}$-$C_{14}$ alkyl group, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

Suitable anionic surfactants for use herein further include alkyl aryl sulphates. Suitable alkyl aryl sulphates for use herein include water-soluble salts or acids of the formula $ROSO_3M$ wherein R is an aryl, preferably a benzyl, substituted by a $C_6$-$C_{24}$ linear or branched saturated or unsaturated alkyl group, preferably a $C_8$-$C_{20}$ alkyl group and more preferably a $C_{10}$-$C_{16}$ alkyl group and M is H or a cation, e.g., an alkali metal cation (e.g., sodium, potassium, lithium, calcium, magnesium and the like) or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

Suitable anionic surfactants for use herein further include alkoxylated sulphate surfactants. Suitable alkoxylated sulphate surfactants for use herein are according to the formula $RO(A)_mSO_3M$ wherein R is an unsubstituted $C_6$-$C_{24}$ alkyl, hydroxyalkyl or alkyl aryl group, having a linear or branched $C_6$-$C_{24}$ alkyl component, preferably a $C_{12}$-$C_{20}$ alkyl or hydroxyalkyl, more preferably $C_{12}$-$C_{18}$ alkyl or hydroxyalkyl, A is an ethoxy or propoxy or butoxy unit or a mixture thereof, m is greater than zero, typically between 0.5 and 6, more preferably between 0.5 and 3, and M is H or a cation which can be, for example, a metal cation (e.g., sodium, potassium, lithium, calcium, magnesium, etc.), ammonium or substituted-ammonium cation. Alkyl ethoxylated sulphates, alkyl butoxylated sulphates as well as alkyl propoxylated sulphates are contemplated herein. Specific examples of substituted ammonium cations include methyl-, dimethyl-, trimethyl-ammonium and quaternary ammonium cations, such as tetramethyl-ammonium, dimethyl piperdinium and cations derived from alkanolamines such as ethylamine, diethylamine, triethylamine, mixtures thereof, and the like. Exemplary surfactants are $C_{12}$-$C_{18}$ alkyl polyethoxylate (1.0) sulphate ($C_{12}$-$C_{18}E(1.0)SM$), $C_{12}$-$C_{18}$ alkyl polyethoxylate (2.25) sulphate ($C_{12}$-$C_{18}E(2.25)SM$), $C_{12}$-$C_{18}$ alkyl polyethoxylate (3.0) sulphate ($C_{12}$-$C_{18}E(3.0)SM$), and $C_{12}$-$C_{18}$ alkyl polyethoxylate (4.0) sulphate ($C_{12}$-$C_{18}E(4.0)SM$), wherein M is conveniently selected from sodium and potassium.

Suitable anionic surfactants for use herein further include alkyl sulphonates. Suitable alkyl sulphonates for use herein include water-soluble salts or acids of the formula $RSO_3M$ wherein R is a $C_6$-$C_{20}$ linear or branched, saturated or unsaturated alkyl group, preferably a $C_8$-$C_{18}$ alkyl group and more preferably a $C_8$-$C_{12}$ linear or branched alkyl group, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

Suitable anionic surfactants for use herein further include alkyl aryl sulphonates. Suitable alkyl aryl sulphonates for use herein include water-soluble salts or acids of the formula $RSO_3M$ wherein R is an aryl, preferably a benzyl, substituted by a $C_6$-$C_{20}$ linear or branched saturated or unsaturated alkyl group, preferably a $C_8$-$C_{18}$ alkyl group and more preferably a $C_9$-$C_{14}$ alkyl group, and M is H or a cation, e.g., an alkali metal cation (e.g., sodium, potassium, lithium, calcium, magnesium and the like) or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

Particularly suitable alkyl sulphonates include $C_{14}$-$C_{17}$ paraffin sulphonate like Hostapur® SAS commercially available from Hoechst. An example of commercially available alkyl aryl sulphonate is Lauryl aryl sulphonate from Su.Ma. Particularly preferred alkyl aryl sulphonates are alkyl benzene sulphonates commercially available under trade name Nansa® available from Albright&Wilson.

Suitable anionic surfactants for use herein further include alkoxylated sulphonate surfactants. Suitable alkoxylated sulphonate surfactants for use herein are according to the formula $R(A)_mSO_3M$ wherein R is an unsubstituted $C_6$-$C_{20}$ alkyl, hydroxyalkyl or alkyl aryl group, having a linear or branched $C_6$-$C_{20}$ alkyl component, preferably a $C_{12}$-$C_{20}$ alkyl or hydroxyalkyl, more preferably $C_{12}$-$C_{18}$ alkyl or hydroxyalkyl, A is an ethoxy or propoxy or butoxy unit, m is greater than zero, typically between 0.5 and 6, more preferably between 0.5 and 3, and M is H or a cation which can be, for example, a metal cation (e.g., sodium, potassium, lithium, calcium, magnesium, etc.), ammonium or substituted-ammonium cation. Alkyl ethoxylated sulphonates, alkyl butoxylated sulphonates as well as alkyl propoxylated sulphonates are contemplated herein. Specific examples of substituted ammonium cations include methyl-, dimethyl-, trimethyl-ammonium and quaternary ammonium cations, such as tetramethyl-ammonium, dimethyl piperdinium and cations derived from alkanolamines such as ethylamine, diethylamine, triethylamine, mixtures thereof, and the like. Exemplary surfactants are $C_{12}$-$C_{18}$ alkyl polyethoxylate (1.0) sulphonate ($C_{12}$-$C_{18}E(1.0)SM$), $C_{12}$-$C_{18}$ alkyl polyethoxylate (2.25) sulphonate ($C_{12}$-$C_{18}E(2.25)SM$), $C_{12}$-$C_{18}$ alkyl polyethoxylate (3.0) sulphonate ($C_{12}$-$C_{18}E(3.0)SM$), and $C_{12}$-$C_{18}$ alkyl polyethoxylate (4.0) sulphonate ($C_{12}$-$C_{18}E(4.0)SM$), wherein M is conveniently selected from sodium and potassium. Particularly suitable alkoxylated sulphonates include alkyl aryl polyether sulphonates like Triton X-200® commercially available from Union Carbide.

Suitable anionic surfactants for use herein further include $C_6$-$C_{20}$ alkyl alkoxylated linear or branched diphenyl oxide disulphonate surfactants. Suitable $C_6$-$C_{20}$ alkyl alkoxylated linear or branched diphenyl oxide disulphonate surfactants for use herein are according to the following formula:

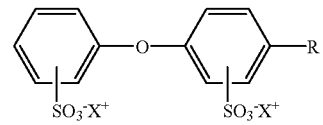

wherein R is a $C_6$-$C_{20}$ linear or branched, saturated or unsaturated alkyl group, preferably a $C_6$-$C_{18}$ alkyl group and more preferably a $C_6$-$C_{14}$ alkyl group, and X+ is H or a cation, e.g., an alkali metal cation (e.g., sodium, potassium, lithium, calcium, magnesium and the like). Particularly suitable $C_6$-$C_{20}$ alkyl alkoxylated linear or branched diphenyl oxide disulphonate surfactants to be used herein are the $C_{12}$ branched di phenyl oxide disulphonic acid and $C_{16}$ linear di phenyl oxide disulphonate sodium salt respectively commercially available by DOW under the trade name Dowfax 2A1® and Dowfax 8390®.

Other suitable anionic surfactants for use herein include alkyl-carboxylates. Other anionic surfactants can include salts (including, for example, sodium, potassium, ammonium, and substituted ammonium salts such as mono-, di- and triethanolamine salts) of soap, $C_8$-$C_{24}$ olefinsulfonates, sulfonated polycarboxylic acids prepared by sulfonation of the pyrolyzed product of alkaline earth metal citrates, e.g., as described in British patent specification No. 1,082,179; acyl glycerol sulfonates, fatty oleyl glycerol sulfates, alkyl phenol ethylene oxide ether sulfates, alkyl phosphates, isethionates such as the acyl isethionates, N-acyl taurates, alkyl succinamates and sulfosuccinates, monoesters of sulfosuccinate (especially saturated and unsaturated $C_{12}$-$C_{18}$ monoesters)

diesters of sulfosuccinate (especially saturated and unsaturated $C_6$-$C_{14}$ diesters), acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula RO(CH$_2$CH$_2$O)$_k$CH$_2$COO-M$^+$ wherein R is a $C_8$-$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

In one preferred embodiment, preferred anionic surfactants for use herein are the C8-C16 alkyl sulfonates, C8-C16 alkyl sulfates, including branched alkyl sulphates, C8-C16 alkyl alkoxylated sulfates (e.g., C8-C16 alkyl ethoxylated sulfates), C8-C16 alkyl alkoxylated sulphonates and mixtures thereof. Such anionic surfactants are preferred herein as it has been found that they contribute to the disinfecting properties of a disinfecting composition herein. For example, C8-C16 alkyl sulfate acts by disorganizing the bacteria cell membrane, inhibiting enzymatic activities, interrupting the cellular transport and/or denaturing cellular proteins. Indeed, it is speculated that the improved disinfecting performance further associated with the addition of an anionic surfactant, especially a C8-C16 alkyl sulfonate, a C8-C16 alkyl sulfate and/or a C8-C16 alkyl alkoxylated sulfate, in a composition according to the present invention, is likely due to multiple mode of attack of said surfactant against the bacteria.

In a second preferred embodiment, the anionic surfactant is selected from the group consisting of: $C_{6\text{-}24}$ alkyl sulphates; $C_{6\text{-}24}$ alkyl aryl sulphates; $C_{6\text{-}24}$ alkyl alkoxylated sulphates; $C_{6\text{-}24}$ alkyl sulphonates, including paraffin sulphonates; $C_{6\text{-}24}$ alkyl aryl sulphonates; $C_{6\text{-}24}$ alkyl alkoxylated sulphonates; $C_6$-$C_{24}$ alkyl alkoxylated linear or branched diphenyl oxide disulphonates; naphthalene sulphonates; and mixtures thereof. More preferably the anionic surfactant is selected from the group consisting of : $C_{6\text{-}24}$ alkyl sulphonates; $C_{6\text{-}24}$ alkyl sulphates; $C_{6\text{-}24}$ alkyl alkoxylated sulphates; $C_{6\text{-}24}$ alkyl aryl sulphonates; and mixtures thereof. Even more preferably the anionic surfactant for use herein is a paraffin sulphonate. Most preferably the anionic surfactant for use herein is a $C_{14}$-$C_{17}$ paraffin sulphonate.

In a third preferred embodiment the anionic surfactant is a branched alkyl sulphate surfactant. Branched alkyl sulphate is herein defined to mean a an alkyl sulfate comprising a sulfate group and a carbon chain of preferably from 2 to 20, more preferably from 2 to 16, most preferably from 2 to 8 carbon atoms. The carbon chain of the branched alkyl sulfate comprises at least one branching group attached to the carbon chain. The branching group is selected from the group consisting of an alkyl group having from 1 to 20, more preferably from 1 to 10 and most preferably from 1 to 4 carbon atoms. The branching group may be located at any position along the alkyl chain of the branched alkyl sulfate. More preferably the branching group is located at position from 1 to 4 along the alkyl chain. The sulfate group can be at any point along the length of the alkyl chain, most preferable at a terminus.

Suitable preferred branched alkyl sulfates include those available from Albright & Wilson under the tradename Empicol 0585/A.

Nonionic Surfactant

Suitable nonionic surfactants for use herein are fatty alcohol ethoxylates and/or propoxylates which are commercially available with a variety of fatty alcohol chain lengths and a variety of ethoxylation degrees. Indeed, the HLB values of such alkoxylated nonionic surfactants depend essentially on the chain length of the fatty alcohol, the nature of the alkoxylation and the degree of alkoxylation. Surfactant catalogues are available which list a number of surfactants, including nonionics, together with their respective HLB values. Preferred nonionic surfactants for one embodiment are those having an average HLB from 8 to 20, more preferably from 10 to 18, most preferably from 11 to 16. These hydrophobic nonionic surfactants have been found to provide good grease cutting properties.

Preferred hydrophobic nonionic surfactants for use in the compositions according to the present invention are surfactants having an HLB below 16 and being according to the formula RO-(C$_2$H$_4$O)$_n$(C$_3$H$_6$O)$_m$H, wherein R is a $C_6$ to $C_{22}$ alkyl chain or a $C_6$ to $C_{28}$ alkyl benzene chain, and wherein n+m is from 0 to 20 and n is from 0 to 15 and m is from 0 to 20, preferably n+m is from 1 to 15 and, n and m are from 0.5 to 15, more preferably n+m is from 1 to 10 and, n and m are from 0 to 10. The preferred R chains for use herein are the $C_8$ to $C_{22}$ alkyl chains. Accordingly, suitable hydrophobic nonionic surfactants for use herein are Dobanol® 91-2.5 (HLB=8.1; R is a mixture of C9 and $C_{11}$ alkyl chains, n is 2.5 and m is 0), or Lutensol® TO3 (HLB=8; R is a $C_{13}$ alkyl chains, n is 3 and m is 0), or Lutensol® AO3 (HLB=8; R is a mixture of $C_{13}$ and $C_{15}$ alkyl chains, n is 3 and m is 0), or Tergitol® 25L3 (HLB=7.7; R is in the range of $C_{12}$ to $C_{15}$ alkyl chain length, n is 3 and m is 0), or Dobanol® 23-3 (HLB=8.1; R is a mixture of $C_{12}$ and $C_{13}$ alkyl chains, n is 3 and m is 0), or Dobanol® 23-2 (HLB=6.2; R is a mixture of $C_{12}$ and $C_{13}$ alkyl chains, n is 2 and m is 0), or Dobanol® 45-7 (HLB=11.6; R is a mixture of $C_{14}$ and $C_{15}$ alkyl chains, n is 7 and m is 0) Dobanol® 23-6.5 (HLB=11.9; R is a mixture of $C_{12}$ and $C_{13}$ alkyl chains, n is 6.5 and m is 0), or Dobanol® 25-7 (HLB=12; R is a mixture of $C_{12}$ and $C_{15}$ alkyl chains, n is 7 and m is 0), or Dobanol® 91-5 (HLB=11.6; R is a mixture of $C_9$ and $C_{11}$ alkyl chains, n is 5 and m is 0), or Dobanol® 91-6 (HLB=12.5 ; R is a mixture of $C_9$ and $C_{11}$ alkyl chains, n is 6 and m is 0), or Dobanol® 91-8 (HLB=13.7 ; R is a mixture of $C_9$ and $C_{11}$ alkyl chains, n is 8 and m is 0), Dobanol® 91-10 (HLB=14.2; R is a mixture of $C_9$ to $C_{11}$ alkyl chains, n is 10 and m is 0), or mixtures thereof. Preferred herein are Dobanol® 91-2.5 , or Lutensol® TO3, or Lutensol® AO3, or Tergitol® 25 L3, or Dobanol® 23-3, or Dobanol® 23-2, or mixtures thereof. These Dobanol® surfactants are commercially available from SHELL. These Lutensol® surfactants are commercially available from BASF and these Tergitol® surfactants are commercially available from UNION CARBIDE.

In a preferred embodiment the nonionic surfactant herein is an alkoxylated nonionic surfactant according to the formula RO—(A)$_n$H, wherein : R is a $C_6$ to $C_{22}$, preferably a $C_8$ to $C_{22}$, more preferably a $C_9$ to $C_{14}$ alkyl chain, or a $C_6$ to $C_{28}$ alkyl benzene chain; A is an ethoxy or propoxy or butoxy unit; and wherein n is from 0 to 20, preferably from 1 to 15 and, more preferably from 2 to 15 even more preferably from 2 to 12 and most preferably from 4 to 10. Preferred R chains for use herein are the $C_8$ to $C_{22}$ alkyl chains. Even more preferred R chains for use herein are the $C_9$ to $C_{12}$ alkyl chains. Ethoxy/butoxylated, ethoxy/propoxylated, butoxy/propoxylated and ethoxy/butoxy/propoxylated nonionic surfactants may also be used herein. Preferred alkoxylated nonionic surfactants are ethoxylated nonionic surfactants.

Suitable alkylpolysaccharides for use herein are disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group. For acidic or alkaline cleaning compositions/solutions suitable for use in no-rinse methods, the preferred alkyl polysaccharide preferably comprises a broad distribution of chain lengths, as these provide the best combination of wetting, cleaning, and low residue upon drying. This "broad distribution" is defined by at least about 50% of the chain-length mixture comprising from about 10 carbon atoms to about 16 carbon atoms. Preferably, the alkyl group of the alkyl polysaccharide consists of a mixtures of chainlength, preferably from about 6 to about 18 carbon atoms, more preferably from about 8 to about 16 carbon atoms, and hydrophilic group containing from about one to about 1.5 saccharide, preferably glucoside, groups per molecule. This "broad chainlength distribution" is defined by at least about 50% of the chainlength mixture comprising from about 10 carbon atoms to about 16 carbon atoms. A broad mixture of chain lengths, particularly $C_8$-$C_{16}$, is highly desirable relative to narrower range chain length mixtures, and particularly versus lower (i.e., $C_8$-$C_{10}$ or $C_8$-$C_{12}$) chainlength alkyl polyglucoside mixtures. It is also found that the preferred $C_8$-$_{16}$ alkyl polyglucoside provides much improved perfume solubility versus lower and narrower chainlength alkyl polyglucosides, as well as other preferred surfactants, including the $C_8$-$C_{14}$ alkyl ethoxylates. Any reducing saccharide containing 5 or 6 carbon atoms can be used, e.g., glucose, galactose and galactosyl moieties can be substituted for the glucosyl moieties. (optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6- positions on the preceding saccharide units. The glycosyl is preferably derived from glucose.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from 8 to 18, preferably from 10 to 16, carbon atoms. Preferably, the alkyl group is a straight-chain saturated alkyl group. The alkyl group can contain up to about 3 hydroxyl groups and/or the polyalkyleneoxide chain can contain up to about 10, preferably less than 5, alkyleneoxide moieties. Suitable alkyl polysaccharides are octyl, nonyidecyl, undecyidodecyl, tridecyl, tetradecyl, pentadecyl, hexadecyl, heptadecyl, and octadecyl, di-, tri-, tetra-, penta-, and hexaglucosides and/or galatoses. Suitable mixtures include coconut alkyl, di-, tri-, tetra-, and pentaglucosides and tallow alkyl tetra-, penta- and hexaglucosides.

To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-,3-, 4- and/or 6-position, preferably predominantly the 2-position.

In the alkyl polyglycosides, the alkyl moieties can be derived from the usual sources like fats, oils or chemically produced alcohols while their sugar moieties are created from hydrolyzed polysaccharides. Alkyl polyglycosides are the condensation product of fatty alcohol and sugars like glucose with the number of glucose units defining the relative hydrophilicity. As discussed above, the sugar units can additionally be alkoxylated either before or after reaction with the fatty alcohols. Such alkyl polyglycosides are described in detail in WO 86/05199 for example. Technical alkyl polyglycosides are generally not molecularly uniform products, but represent mixtures of alkyl groups and mixtures of monosaccharides and different oligosaccharides. Alkyl polyglycosides (also sometimes referred to as "APG's") are preferred for the purposes of the invention since they provide additional improvement in surface appearance relative to other surfactants. The glycoside moieties are preferably glucose moieties. The alkyl substituent is preferably a saturated or unsaturated alkyl moiety containing from about 8 to about 18 carbon atoms, preferably from about 8 to about 10 carbon atoms or a mixture of such alkyl moieties. $C_8$-$C_{16}$ alkyl polyglucosides are commercially available (e.g., Simusol® surfactants from Seppic Corporation, 75 Quai d'Orsay, 75321 Paris, Cedex 7, France, and Glucopon®425 available from Henkel. However, it has been found that purity of the alkyl polyglucoside can also impact performance, particularly end result for certain applications, including daily shower product technology. In the present invention, the preferred alkyl polyglucosides are those which have been purified enough for use in personal cleansing. Most preferred are "cosmetic grade" alkyl polyglucosides, particularly $C_8$ to $C_{16}$ alkyl polyglucosides, such as Plantaren 2000®, Plantaren 2000 N®, and Plantaren 2000 N UP®, available from Henkel Corporation (Postfach 101100, D 40191 Dusseldorf, Germany).

Amphoteric/Zwitterionic Surfactant

Suitable amphoteric surfactants for use herein include amine oxides having the following formula $R_1 R_2R_3NO$ wherein each of R1, R2 and R3 is independently a saturated substituted or unsubstituted, linear or branched hydrocarbon chains of from 1 to 30 carbon atoms. Preferred amine oxide surfactants to be used according to the present invention are amine oxides having the following formula $R_1 R_2R_3NO$ wherein R1 is an hydrocarbon chain comprising from 1 to 30 carbon atoms, preferably from 6 to 20, more preferably from 8 to 16, most preferably from 8 to 12, and wherein R2 and R3 are independently substituted or unsubstituted, linear or branched hydrocarbon chains comprising from 1 to 4 carbon atoms, preferably from 1 to 3 carbon atoms, and more preferably are methyl groups. R1 may be a saturated substituted or unsubstituted linear or branched hydrocarbon chain.

Suitable amine oxides for use herein are for instance natural blend C8-C10 amine oxides as well as C12-C16 amine oxides commercially available from Hoechst and Clariant.

Suitable zwitterionic surfactants for use herein contain both cationic and anionic hydrophilic groups on the same molecule at a relatively wide range of pH's. The typical cationic group is a quaternary ammonium group, although other positively charged groups like phosphonium, imidazolium and sulfonium groups can be used. The typical anionic hydrophilic groups are carboxylates and sulfonates, although other groups like sulfates, phosphonates, and the like can be used. A generic formula for some zwitterionic surfactants to be used herein is

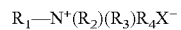

$R_1$—$N^+(R_2)(R_3)R_4X^-$ wherein $R_1$ is a hydrophobic group; $R_2$ and $R_3$ are each $C_1$-$C_4$ alkyl, hydroxy alkyl or other substituted alkyl group which can also be joined to form ring structures with the N; $R_4$ is a moiety joining the cationic nitrogen atom to the hydrophilic group and is typically an alkylene, hydroxy alkylene, or polyalkoxy group containing from 1 to 10 carbon atoms; and X is the hydrophilic group which is preferably a carboxylate or sulfonate group. Preferred hydrophobic groups $R_1$ are alkyl groups containing from 1 to 24, preferably less than 18, more preferably less than 16 carbon atoms. The hydrophobic group can contain unsaturation and/or substituents and/or linking groups such as aryl groups, amido groups, ester groups and the like. In general, the simple alkyl groups are preferred for cost and stability reasons.

Highly preferred zwitterionic surfactants include betaine and sulphobetaine surfactants, functionalized betaines such as acyl betaines, alkyl imidazoline alanine betaines, glycine betaines, derivatives thereof and mixtures thereof. Said betaine or sulphobetaine surfactants are preferred herein as they help disinfection by increasing the permeability of the bacterial cell wall, thus allowing other active ingredients to enter the cell.

Furthermore, due to the mild action profile of said betaine or sulphobetaine surfactants, they are particularly suitable for the cleaning of delicate surfaces, e.g., delicate laundry or surfaces in contact with food and/or babies. Betaine and sulphobetaine surfactants are also extremely mild to the skin and/or surfaces to be treated.

Suitable betaine and sulphobetaine surfactants for use herein are the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702,279 and 2,255, 082, incorporated herein by reference. Preferred betaine and sulphobetaine surfactants herein are according to the formula

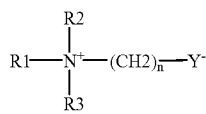

wherein R1 is a hydrocarbon chain containing from 1 to 24 carbon atoms, preferably from 8 to 18, more preferably from 12 to 14, wherein R2 and R3 are hydrocarbon chains containing from 1 to 3 carbon atoms, preferably 1 carbon atom, wherein n is an integer from 1 to 10, preferably from 1 to 6, more preferably is 1, Y is selected from the group consisting of carboxyl and sulfonyl radicals and wherein the sum of R1, R2 and R3 hydrocarbon chains is from 14 to 24 carbon atoms, or mixtures thereof.

Examples of particularly suitable betaine surfactants include C12-C18 alkyl dimethyl betaine such as coconutbetaine and C10-C16 alkyl dimethyl betaine such as laurylbetaine. Coconutbetaine is commercially available from Seppic under the trade name of Amonyl 265®. Laurylbetaine is commercially available from Albright & Wilson under the trade name Empigen BB/L®.

Other specific zwitterionic surfactants have the generic formulas:

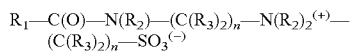

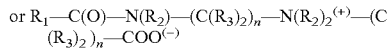

wherein each $R_1$ is a hydrocarbon, e.g. an alkyl group containing from 8 up to 20, preferably up to 18, more preferably up to 16 carbon atoms, each $R_2$ is either a hydrogen (when attached to the amido nitrogen), short chain alkyl or substituted alkyl containing from one to 4 carbon atoms, preferably groups selected from the group consisting of methyl, ethyl, propyl, hydroxy substituted ethyl or propyl and mixtures thereof, preferably methyl, each $R_3$ is selected from the group consisting of hydrogen and hydroxy groups and each n is a number from 1 to 4, preferably from 2 to 3, more preferably 3, with no more than one hydroxy group in any $(C(R_3)_2)$ moiety. The $R_1$ groups can be branched and/or unsaturated. The $R_2$ groups can also be connected to form ring structures. A surfactant of this type is a $C_{10}$-$C_{14}$ fatty acylamidopropylene(hydroxypropylene)sulfobetaine that is available from the Sherex Company under the trade name "Varion CAS sulfobetaine"®.

Peroxygen Bleach

The compositions according to the present invention may comprise a peroxygen bleach as an optional feature.

A preferred peroxygen bleach is hydrogen peroxide, or a water soluble source thereof, or mixtures thereof. As used herein a hydrogen peroxide source refers to any compound which produces hydrogen peroxide when said compound is in contact with water. Suitable water-soluble sources of hydrogen peroxide for use herein include percarbonates, persilicates, persulphates such as monopersulfate, perborates and peroxyacids such as diperoxydodecandioic acid (DPDA), magnesium perphthalic acid and mixtures thereof.

In addition, other classes of peroxides can be used as an alternative to hydrogen peroxide and sources thereof or in combination with hydrogen peroxide and sources thereof. Suitable classes include dialkylperoxides, diacylperoxides, preformed percarboxylic acids, organic and inorganic peroxides and/or hydroperoxides. The most preferred peroxygen bleach is hydrogen peroxide.

The presence of said peroxygen bleach especially hydrogen peroxide, persulfate and the like, in the compositions according to the present invention can contribute to disinfection properties of said compositions. Indeed, said peroxygen bleach may attack the vital function of the micro-organism cells, for example, it may inhibit the assembling of ribosomes units within the cytoplasm of the microorganisms cells. Also said peroxygen bleach like hydrogen peroxide, is an oxidiser that generates hydroxyl free radicals which attack proteins and nucleic acids. Furthermore, the presence of said peroxygen bleach, especially hydrogen peroxide, provides strong stain removal benefits which are particularly noticeable for example in laundry and hard surfaces applications.

Typically, peroxygen bleach or a mixture thereof is present in the compositions according to the present invention at a level of at least 0.01% by weight of the total composition, preferably from 0.1% to 15%, and more preferably from 1% to 10%.

Disinfecting Agent

Another preferred component of the compositions of the present invention is a disinfecting agent. Any suitable known disinfecting agent may be used herein including organic acids, quaternary ammonium compounds, antimicrobial essential oils or actives thereof, or a mixtures thereof.

Preferred therein include organic acids, antimicrobial essential oils or actives thereof, or a mixtures thereof. Preferred organic acids include citric acid, tartaric acid, salicylic acid, lactic acid and mixtures thereof.

Suitable antimicrobial essential oils to be used herein are those essential oils which exhibit antimicrobial activity. By "actives of essential oils", it is meant herein any ingredient of essential oils or natural extracts that exhibit antimicrobial activity. It is speculated that said antimicrobial essential oils and actives thereof act as proteins denaturing agents. Also said antimicrobial oils and actives thereof are compounds which contribute to the safety profile of a composition comprising them when it is used to disinfect any surface. A further advantage of said antimicrobial oils and actives thereof is that they impart pleasant odor to a composition comprising them without the need of adding a perfume.

Such antimicrobial essential oils include, but are not limited to, those obtained from thyme, lemongrass, citrus, lemons, oranges, anise, clove, aniseed, pine, cinnamon, geranium, roses, mint, lavender, citronella, eucalyptus, peppermint, camphor, ajowan, sandalwood, rosmarin, vervain, fleagrass, lemongrass, ratanhiae, cedar, origanum, cypressus, propolis extracts and mixtures thereof. Preferred antimicrobial essential oils to be used herein are thyme oil, clove oil, cinnamon oil, geranium oil, eucalyptus oil, peppermint oil, citronella oil, ajowan oil, mint oil, origanum oil, propolis, cypressus oil cedar , garlic extract or mixtures thereof.

Actives of essential oils to be used herein include, but are not limited to, thymol (present for example in thyme, ajowan), eugenol (present for example in cinnamon and clove), menthol (present for example in mint), geraniol (present for example in geranium and rose, citronella), verbenone (present for example in vervain), eucalyptol and pinocarvone (present in eucalyptus), cedrol (present for example in cedar), anethol (present for example in anise), carvacrol, hinokitiol, berberine, ferulic acid, cinnamic acid, methyl salicylic acid, methyl salycilate, terpineol, limonene and mixtures thereof. Preferred actives of essential oils to be used herein are thymol, eugenol, verbenone, eucalyptol, terpineol, cinnamic acid, methyl salicylic acid, limonene, geraniol, ajolene or mixtures thereof.

Thymol may be commercially available for example from Aldrich, eugenol may be commercially available for example from Sigma, Systems—Bioindustries (SBI)—Manheimer Inc.

Typically, the antimicrobial essential oil or active thereof or mixture thereof is present in the composition at a level of at least 0.001% by weight of the total composition, preferably from 0.006% to 10%, more preferably from 0.01% to 8% and most preferably of from 0.03% to 3%.

It has now been found that combining said antimicrobial essential oil or an active thereof or a mixture thereof with a peroxygen bleach, in a composition, delivers not only excellent immediate disinfecting properties to the surfaces treated with said composition, but also long lasting disinfecting properties. Indeed, it is speculated that peroxygen bleach and said essential oils/actives adsorb on a surface having been treated with said composition and thus reduce or even prevent the contamination of microorganisms over time, typically up to 48 hours after the surface has been treated with said composition, thereby delivering long lasting disinfection. In other words, it is speculated that a microfilm of said active ingredients is deposited on the surface treated with said compositions allowing protection against microorganisms recontamination overtime. Advantageously, this long lasting disinfection benefits is obtained with the compositions of the present invention comprising peroxygen bleach and antimicrobial essential oils/actives even when used under highly diluted conditions, i.e., up to dilution levels of from 1:100 (composition:water).

Excellent long lasting disinfection is obtained by treating a surface with a composition comprising a peroxygen bleach and an antimicrobial essential oil or active thereof as described herein, on a variety of microorganisms, e.g., the growth of Gram positive bacteria like *Staphylococcus aureus*, and Gram negative bacteria like *Pseudomonas aeroginosa* as well as of fungi like *Candida albicans* is reduced or even prevented on a surface having been treated with said composition.

Long lasting disinfection properties of the compositions herein may be measured by the bactericidal activity of said compositions. A test method suitable to evaluate the long lasting bactericidal activity of a composition may be as follow: First, the surfaces (e.g. glass) to be tested are respectively treated with either a composition according to the present invention or a reference composition, e.g., a negative control composed of pure water (for example by spraying the composition directly on the surface or first spraying the composition on a sponge used to clean the surface or when the composition herein is executed in the form of wipe by wiping the surface therewith). After a variable time frame (e.g. 24 hours) each surface is respectively inoculated with bacteria ($10^{6-7}$cfu/slide) cultured in for example TSB (Tryptone Soya Broth) and left typically from a few seconds to 2 hours before evaluating the remaining living bacteria. Then living bacteria (if any) are recovered from the surface (by touching TSA+ neutraliser plates and by re-suspending the bacteria into the neutralisation broth and plating them on agar) and incubated at appropriate temperature, e.g. 37° C. to let them grow typically over night. Finally, a visual grading of the living bacteria is made by comparing side by side the cultures and/or dilutions thereof (e.g. $10^{-2}$ or $10^{-1}$) resulting from the surfaces treated with the compositions according to the present invention and the reference composition.

In a particular embodiment of the present invention, depending on the end use desired with said compositions they may further comprise, as optional ingredients, other antimicrobial compounds that further contribute to the antimicrobial/antibacterial activity of the compositions according to the present invention. Such antimicrobial ingredients include parabens like ethyl paraben, propyl paraben, methyl paraben, glutaraldehyde or mixtures thereof.

Chelating Agent

The compositions herein may further comprise a chelating agent as a preferred optional ingredient. Suitable chelating agents may be any of those known to those skilled in the art such as the ones selected from the group comprising phosphonate chelating agents, aminophosphonate chelating agents, substituted heteroaromatic chelating agents, amino carboxylate chelating agents, other carboxylate chelating agents, polyfunctionally-substituted aromatic chelating agents, biodegradable chelating agents like ethylene diamine N,N'-disuccinic acid, or mixtures thereof.

Suitable phosphonate chelating agents to be used herein include etidronic acid (1-hydroxyethylene-diphosphonic acid (HEDP)), and/or alkali metal ethane 1-hydroxydiphosphonates.

Suitable amino phosphonate chelating agents to be used herein include amino alkylene poly (alkylene phosphonates), nitrilotris(methylene)triphosphonates, ethylene diamine tetra methylene phosphonates, and/or diethylene triamine penta methylene phosphonates. Preferred aminophosphonate chelating agents to be used herein are diethylene triamine penta methylene phosphonates.

These phosphonate/amino phosphonate chelating agents may be present either in their acid form or as salts of different cations on some or all of their acid functionalities. Such phosphonate/amino phosphonate chelating agents are commercially available from Monsanto under the trade name DEQUEST®.

Substituted heteroaromatic chelating agents to be used herein include hydroxypiridine-N-oxide or a derivative thereof.

Suitable hydroxy pyridine N-oxides and derivatives thereof to be used according to the present invention are according to the following formula:

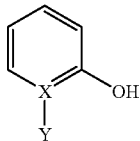

wherein X is nitrogen, Y is one of the following groups oxygen, —CHO, —OH, —(CH2)n—COOH, wherein n is an integer of from 0 to 20, preferably of from 0 to 10 and more preferably is 0, and wherein Y is preferably oxygen. Accordingly particularly preferred hydroxy pyridine N-oxides and derivatives thereof to be used herein is 2-hydroxy pyridine N-oxide. Hydroxy pyridine N-oxides and derivatives thereof may be commercially available from Sigma.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy -3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987 to Hartman and Perkins. Ethylenediamine N,N'-disuccinic acid is, for instance, commercially available under the tradename ssEDDS® from Palmer Research Laboratories. Ethylene diamine N,N'-disuccinic acid is particularly suitable to be used in the compositions of the present invention.

Suitable amino carboxylate chelating agents useful herein include ethylene diamine tetra acetates, diethylene triamine pentaacetates, diethylene triamine pentoacetate (DTPA), N-hydroxyethylethylenediamine triacetates, nitrilotri-acetates, ethylenediamine tetraproprionates, triethylenetetraaminehexa-acetates, ethanoldiglycines, propylene diamine tetracetic acid (PDTA) and methyl glycine di-acetic acid (MGDA), both in their acid form, or in their alkali metal, ammonium, and substituted ammonium salt forms. Particularly suitable to be used herein are diethylene triamine penta acetic acid (DTPA), propylene diamine tetracetic acid (PDTA) which is, for instance, commercially available from BASF under the trade name Trilon FS® and methyl glycine di-acetic acid (MGDA).

Further carboxylate chelating agents to be used herein includes malonic acid, salicylic acid, glycine, aspartic acid, glutamic acid, or mixtures thereof.

Typically, the compositions according to the present invention comprise up to 5% by weight of the total composition of a chelating agent, or mixtures thereof, preferably from 0.01% to 3% by weight and more preferably from 0.01% to 1.5%.

Radical Scavenger

The compositions herein may comprise a radical scavenger as another optional ingredient. Suitable radical scavengers for use herein include the well-known substituted mono and di hydroxy benzenes and derivatives thereof, alkyl- and aryl carboxylates and mixtures thereof. Preferred radical scavengers for use herein include di-tert-butyl hydroxy toluene (BHT), p-hydroxy-toluene, hydroquinone (HQ), di-tert-butyl hydroquinone (DTBHQ), mono-tert-butyl hydroquinone (MTBHQ), tert-butyl-hydroxy anysole (BHA), p-hydroxyanysol, benzoic acid, 2,5-dihydroxy benzoic acid, 2,5-dihydroxyterephtalic acid, toluic acid, catechol, t-butyl catechol, 4-allyl-catechol, 4-acetyl catechol, 2-methoxy-phenol, 2-ethoxy-phenol, 2-methoxy-4-(2-propenyl)phenol, 3,4-dihydroxy benzaldehyde, 2,3-dihydroxy benzaldehyde, benzylamine, 1,1,3-tris(2-methyl-4-hydroxy-5-t-butylphenyl)butane, tert-butyl-hydroxy-anyline, p-hydroxy anyline as well as n-propyl-gallate. Highly preferred for use herein are di-tert-butyl hydroxy toluene, which is for example commercially available from SHELL under the trade name IONOL CP® and/or tert-butyl-hydroxy anysole. These radical scavengers further contribute to the stability of the peroxygen bleach-containing compositions herein.

Typically, the compositions according to the present invention comprise up to 5% by weight of the total composition of a radical scavenger, or mixtures thereof, preferably from 0.002% to 1.5% by weight and more preferably from 0.002% to 1%.

Solvent

The compositions herein may comprise as a preferred optional ingredient a solvent or mixtures thereof. When used, solvents will, advantageously, give an enhanced cleaning to the compositions herein. Suitable solvents for incorporation in the compositions according to the present invention include propylene glycol derivatives such as n-butoxypropanol or n-butoxypropoxypropanol, water-soluble CARBITOL® solvents or water-soluble CELLOSOLVE® solvents. Water-soluble CARBITOL® solvents are compounds of the 2-(2-alkoxyethoxy)ethanol class wherein the alkoxy group is derived from ethyl, propyl or butyl. A preferred water-soluble carbitol is 2-(2-butoxyethoxy)ethanol also known as butyl carbitol. Water-soluble CELLOSOLVE® solvents are compounds of the 2-alkoxyethoxyethanol class, with 2-butoxyethoxyethanol being preferred. Other suitable solvents are benzyl alcohol, methanol, ethanol, isopropyl alcohol and diols such as 2-ethyl-1,3-hexanediol and 2,2,4-trimethyl-1,3-pentanediol, volatile silicones and mixture thereof. Preferred solvents for use herein are n-butoxypropoxypropanol, butyl carbitol®, benzyl alcohol, isopropanol, 1-propanol and mixtures thereof. Most preferred solvents for use herein are butyl carbitol®, benzyl alcohol, 1-propanol and/or isopropanol.

The solvents may typically be present within the compositions according to the invention at a level up to 15% by weight, preferably from 0.5% to 7% by weight of the composition.

pH Buffer

In the embodiment of the present invention wherein the compositions are formulated in the alkaline pH range, typically from 7.5 to 12, the compositions according to the present invention may further comprise a pH buffer or a mixture thereof, i.e. a system composed of a compound or a combination of compounds, whose pH changes only slightly when a strong acid or base is added.

Suitable pH buffers for use herein include borate pH buffer, phosphonate, silicate and mixtures thereof. Suitable borate pH buffers for use herein include alkali metal salts of borates and alkyl borates and mixtures thereof. Suitable borate pH buffers to be used herein are alkali metal salts of borate, metaborate, tetraborate, octoborate, pentaborate, dodecaboron, borontrifluoride and/or alkyl borate containing from 1 to 12 carbon atoms, and preferably from 1 to 4. Suitable alkyl borate includes methyl borate, ethyl borate and propyl borate. Particularly preferred herein are the alkali metal salts of metaborate (e.g. sodium metaborate), tetraborate (e.g., sodium tetraborate decahydrate) or mixtures thereof.

Boron salts like sodium metaborate and sodium tetraborate are commercially available from Borax and Societa Chimica Larderello under the trade name sodium metaborate® and Borax®.

The pH of the composition can also be adjusted to an acidic pH and/or buffered at that pH using any suitable acidifying agent, for example organic acids for example citric acid, tartaric acid, lactic acid and mixtures thereof.

Typically, the compositions according to the present invention may comprise up to 15% by weight of the total composition of a pH buffer, or mixtures thereof, preferably from 0.01% to 10%, more preferably from 0.01% to 5% and most preferably from 0.1% to 3%.

Packaging Form of the Wet Wipes

In a preferred embodiment according to the present invention, the wet wipes are packaged in the container in any convenient configuration which allows easy removal of a single or multiple wet wipe from the container. Preferably the wipes are packaged in rolls, stacks or piles. More preferably the wipes are provided in a stacked configuration which may comprise any number of wipes. Typically, the stack comprises from 2 to 150, more preferably from 5 to 100, most preferably from 10 to 60 wipes. Moreover the wipes may be provided folded or unfolded. Most preferably, the wipes are stacked in a folded configuration.

Process of Treating a Surface

In a preferred embodiment, the present invention encompasses a process of cleaning and/or disinfecting a surface, preferably a hard surface, comprising the step of contacting, preferably wiping, said surface with a substrate which incorporates a composition as described herein.

In a preferred embodiment of the present application, said process comprises the steps of contacting parts of said surface, more preferably soiled parts of said surface, with said substrate which incorporates a composition as described herein.

In another preferred embodiment said process, after contacting said surface with said substrate which incorporates a composition as described herein, further comprises the step of imparting mechanical action to said surface using said substrate which incorporates a composition as described herein. By "mechanical action" it is meant herein, agitation of the wet wipe on the surface, as for example rubbing the surface using the wet wipe.

By "surface", it is meant herein any surface including animate surface like human skin, mouth, teeth, and inanimate surfaces. Inanimate surfaces include, but are not limited to, hard-surfaces typically found in houses like kitchens, bathrooms, or in car interiors, e.g., tiles, walls, floors, chrome, glass, smooth vinyl, any plastic, plastified wood, table top, sinks, cooker tops, dishes, sanitary fittings such as sinks, showers, shower curtains, wash basins, WCs and the like, as well as fabrics including clothes, curtains, drapes, bed linens, bath linens, table cloths, sleeping bags, tents, upholstered furniture and the like, and carpets. Inanimate surfaces also include household appliances including, but not limited to, refrigerators, freezers, washing machines, automatic dryers, ovens, microwave ovens, dishwashers and so on.

Experimental Data

The tensile strength and biodegradability of the substrate of the present invention was compared against substrates found in the prior art using the test methods described above.

| Substrate | Loading factor | Wet tensile strength (N/inch) | | Anaerobic disintegration (dry substrate) % weight loss | | |
|---|---|---|---|---|---|---|
| | | MD | CD | Week 1 | Week 2 | Week 4 |
| 100% hydroentangled viscose[1] | 3.0 | 32 | 10 | 100 | 100 | 100 |
| Walkisoft[2] | 4.0 | 7.0 | 6.3 | 60.3 | 85.1 | 87.1 |
| Dover[3] | 3.25 | 10 | 5 | 43.2 | 61 | 68.3 |
| Tesco[4] | approx. 3.5 | 12.5 | 6.5 | na | na | approx. 80% |
| Kao[5] | approx 1.5 | 1 | 5 | 100% | 100% | 100% |

[1]Substrate according to the present invention
[2]Air-laid latex bond substrate from Walkisoft (UPM-Kymmene Group). This substrate comprises 85% cellulosic fibres and 15% Styrene-butadiene resin as a binder
[3]Air-laid latex bond substrate made by Procter & Gamble. This substrate comprises 70% cellulose natural fibres, 15% synthetic fibres and 15% Styrene-butadiene resin as a binder
[4]Wet Wipe sold under the Tesco Toilet Wipes by Tesco ltd. The Tesco substrate is resin bonded and comprises 40% hydroentangled viscose, 33% woodpulp and 22% polyethylene tetraphthalate (PET)
[5]Wet Wipe sold under the Quickle bathroom wipes by Kao. The Kao substrate comprises 100% wood pulp, obtained by a wet-laid consolidation process.

EXAMPLES

Provided below are, non-limiting, examples A to D of cleaning compositions which may be incorporated into the wipes of the present invention.

| Ingredient | A % w/w | B % w/w | C % w/w | D % w/w |
|---|---|---|---|---|
| Ethanol | 9.4 | 9.4 | 9.5 | 9.5 |
| C12-14 Amine Oxide | 0.4 | 0.4 | — | — |
| Propylene Glycol Butyl Ether | 0.55 | 0.55 | — | — |
| Diethylene Glycol Butyl Ether | 0.55 | 0.55 | — | — |
| Polypropylene glycol mono butyl ether | 0.25 | 0.25 | — | — |
| Silicone | 0.003 | 0.003 | 0.003 | 0.003 |
| Citric acid | 0.75 | 0.75 | — | — |
| Sodium hydroxide | 0.1 | — | — | — |
| Hydrogen Peroxide | — | 1.00 | — | — |
| Salicylic acid | — | 0.03 | — | — |
| BHT | — | 0.01 | — | — |
| Geraniol | — | 0.0375 | 0.1 | 0.1 |
| Thymol | — | 0.025 | — | — |
| C12-14 Betaine | — | — | 0.2 | — |
| Dobanol 91-8 | — | — | 0.8 | 0.8 |
| C8 alkyl sulphate branched | — | — | 0.6 | 0.6 |
| C10 Amine Oxide | — | — | — | 0.2 |
| Lactic acid | — | — | 1.5 | 1.5 |
| Perfume | 0.18 | 0.0375 | 0.15 | 0.15 |
| Water | 87.82 | 86.95 | 87.15 | 87.15 |

What is claimed is:

1. A flushable wet wipe suitable for cleaning a hard surface comprising a substrate having tensile strength of at least 5 N/inch and which is biodegradable, wherein said substrate incorporates a cleaning composition having a pH in the range of from 7 to 13 comprising an organic acid selected from the group consisting of citric acid, tartaric acid, lactic acid, and mixtures thereof.

2. A flushable wet wipe suitable for cleaning a hard surface according to claim 1 wherein the substrate has tensile strength of at least 5 N/inch in the cross direction.

3. A flushable wet wipe according to claim 1 wherein the substrate has tensile strength of at least 8 N/inch.

4. A flushable wet wipe according to claim 3 wherein the substrate has tensile strength of at least 10 N/inch.

5. A flushable wet wipe according to claim 1 wherein the substrate has an absorption capacity of at least 6 grams of water per gram of substrate.

6. A flushable wet wipe according to claim 1 wherein at least 95% disintegration of the wipe in anaerobic conditions is achieved after 4 weeks of anaerobic digestion.

7. A flushable wet wipe according to claim 1 wherein the substrate is substantially entirely composed of man-made fibres.

8. A flushable wet wipe suitable for cleaning a hard surface comprising a substrate having tensile strength of at least 5 N/inch and which is biodegradable, wherein said substrate incorporates a cleaning composition comprising an organic acid selected from the group consisting of citric acid, tartaric acid, lactic acid, and mixtures thereof; and further, wherein the substrate is substantially entirely composed of substantially 100% hydroentangled man-made regenerated cellulosic fibres and contains no chemical binders.

9. A flushable wet wipe suitable for cleaning a hard surface comprising a substrate having tensile strength of at least 5 N/inch and which is biodegradable, wherein said substrate incorporates a cleaning composition comprising an organic acid selected from the group consisting of citric acid, tartaric acid, lactic acid, and mixtures thereof; and further, wherein the cleaning composition comprises a disinfecting component selected from the group consisting of thyme oil, lemon grass oil, lemon oil, orange oil, anise oil, clove oil, aniseed oil, pine oil, cinnamon oil, geranium oil, rose oil, mint oil, lavender oil, citronella oil, eucalyptus oil, peppermint oil, camphor, ajowan oil, sandalwood oil, rosmarin, vervain, fleagrass, ratanhiae, cedar, garlic extract, origanum oil, cypressus oil, propolis, thymol, eugenol, menthol, geraniol, ajolene, verbenone, eucalyptol, pinocarvone, cedrol, anethol, carvacrol, hinokitiol, berberine, ferulic acid, cinnamic acid, methyl salicylic acid, methyl salicylate, terpineol, limonene, and mixtures thereof.

10. A flushable wet wipe according to claim 9 wherein the disinfecting component is selected from the group consisting of thyme oil, clove oil, cinnamon oil, geranium oil, eucalyptus oil, peppermint oil, citronella oil, ajowan oil, mint oil, origanum oil, propolis, cypressus oil, cedar, garlic extract, thymol, eugenol, verbenone, eucalyptol, terpineol, cinnamic acid, methyl salicylic acid, limonene, geraniol, ajolene, and mixtures thereof.

11. A process of cleaning a hard surface comprising the step of contacting the surface with a wet wipe according to claim 1.

12. A process according to claim 11 wherein the surface is a hard surface.

13. A process according to claim 12 wherein the hard surface is a lavatory surface.

14. A flushable wet wipe according to claim 1 wherein the substrate has a loading factor of at least 1.5 grams of cleaning composition per gram of substrate.

15. A flushable wet wipe according to claim 14 wherein the substrate has tensile strength of at least 8 N/inch.

16. A flushable wet wipe according to claim 15 wherein the substrate has tensile strength of at least 10 N/inch.

17. A flushable wet wipe according to claim 14 wherein the substrate has an absorption capacity of at least 6 grams of water per gram of substrate.

18. A flushable wet wipe according to claim 14 wherein at least 95% disintegration of the wipe in anaerobic conditions is achieved after 4 weeks of anaerobic digestion as measured according to the test method described herein.

19. A flushable wet wipe according to claim 14 wherein the substrate is substantially entirely composed of man-made fibres.

20. A flushable wet wipe according to claim 19 wherein the substrate is substantially entirely composed of substantially 100% hydroentangled man-made regenerated cellulosic fibres.

21. A flushable wet wipe according to claim 9 wherein the substrate has a loading factor of at least 1.5 grams of cleaning composition per gram of substrate.

22. A flushable wet wipe according to claim 21 wherein the disinfecting component is selected from the group consisting of thyme oil, clove oil, cinnamon oil, geranium oil, eucalyptus oil, peppermint oil, citronella oil, ajowan oil, mint oil, origanum oil, propolis, cypressus oil, cedar, garlic extract, thymol, eugenol, verbenone, eucalyptol, terpineol, cinnamic acid, methyl salicylic acid, limonene, geraniol, ajolene, and mixtures thereof.

23. A process of cleaning a hard surface comprising the step of contacting the surface with a wet wipe according to claim 14.

24. A process according to claim 23 wherein the surface is a hard surface.

25. A process according to claim 24 wherein the hard surface is a lavatory surface.

* * * * *